(12) United States Patent
Jia

(10) Patent No.: US 6,395,311 B2
(45) Date of Patent: *May 28, 2002

(54) MULTICOMPONENT BIOLOGICAL VEHICLE

(75) Inventor: Qi Jia, Arvada, CO (US)

(73) Assignee: Univera Pharmaceuticals, Inc., Broomfield, CO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/301,892

(22) Filed: Apr. 29, 1999

Related U.S. Application Data
(60) Provisional application No. 60/083,420, filed on Apr. 29, 1998.

(51) Int. Cl.[7] ............... A61K 33/14; A61K 33/42; A61K 47/36
(52) U.S. Cl. ............ 424/744; 424/744; 424/734; 424/725; 424/677; 424/678; 424/464; 514/772.2; 514/783; 514/773
(58) Field of Search ............ 424/464, 744, 424/734, 725, 722, 677, 678; 514/772.2, 783, 773

(56) References Cited

U.S. PATENT DOCUMENTS

| | | | |
|---|---|---|---|
| 4,598,069 A | * 7/1986 | Hikino et al. | 514/54 |
| 5,536,506 A | * 7/1996 | Majeed et al. | 424/464 |
| 5,589,182 A | * 12/1996 | Tashiro et al. | 424/195.1 |
| 5,708,038 A | 1/1998 | Davis | |

FOREIGN PATENT DOCUMENTS

| | | | |
|---|---|---|---|
| EP | 0861595 | * 2/1998 | A23F/3/34 |
| WO | WO 96/40182 | 12/1996 | |

OTHER PUBLICATIONS

Davis et al. (1991) JAPMA 81:1.
Grindlay and Reynolds (1986) J. of Ethnopharmacology 16:117–151.
Hart et al. (1988) J. of Ethnopharmacology 23:61–71.
Hoffman et al. (1984) Am. J. Physiol. 274:E772.
Kaplan et al. (1995) Physiol. Res. 44:39–45.
Laudanna et al. (1997) J. Biol. Chem. 272:24141.
Reitman and Frankel (1957) Determination of Transaminases 28:56–63.
Si et al. (1997) Immunopharmacology 36:1.
Song et al. (1997) Nature 388:275.
Wolf et al. (1993) The Journal of Investigative Dermatology 100:254–259.
Hirata and Suga (1977) Z. Naturforsch 32c:731–734.

\* cited by examiner

*Primary Examiner*—Diana Dudash
*Assistant Examiner*—Shahnam Sharareh
(74) *Attorney, Agent, or Firm*—Swanson & Bratschun, L.L.C.

(57) ABSTRACT

The present invention provides a novel vehicle for the delivery of biologically active agents. The vehicle, Maxcell™, is formulated from a novel combination of natural plant extracts and is comprised of Aloe vera polysaccharide fraction Immuno-10, cAMP, piperine, calcium phosphate and glycyrrhizinic acid.

14 Claims, 8 Drawing Sheets

MULTICOMPONENT BIOLOGICAL VEHICLE

RELATED APPLICATIONS

This application claims priority from U.S. Provisional patent application Ser. No. 60/083,420, filed Apr. 29, 1998, entitled "Multicomponent Biological Vehicle."

FIELD OF INVENTION

The present invention relates generally to a vehicle for the delivery of biologically active agents. In particular this invention includes a biological vehicle formulated from a novel combination of plant extracts that can be used for the delivery of a variety of biologically active agents. Also included in this invention are methods for using the vehicle and formulations containing the vehicle.

BACKGROUND OF THE INVENTION

A vehicle is a substance, usually without biological activity, which is used as a medium for the administration of pharmacologic agents. Ideally a vehicle should be nonirritating and compatible with common medications. Criteria for vehicle selection include solubility of the active agent in the vehicle and the ability of the vehicle to penetrate physical barriers such as the stratum corneum and the lipid portion of the cell membrane. Consideration must also be given to any interactions between the vehicle and the active agent, the efficiency with which the vehicle releases the incorporated active ingredient, the molecular size and the composition of the vehicle. Traditional vehicles for subcutaneous administration include oils which tend to be irritating.

Occasionally, a vehicle will have a synergistic effect, such that the final sum total of the activity in each system is greater than the sum of the components. This is highly desirable in that less of the pharmacologic agent can be used to achieve the same effect, thereby reducing or eliminating any side effects associated with higher dosages.

Aloe is an intricate plant which contains many biologically active substances. (Cohen et al. (1992) in *Wound Healing/Biochemical and Clinical Aspects*, 1st ed. W B Saunders, Philadelphia). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity, (see, e.g., Yagi et al. (1977) Z. Naturforsch 32c:731–734), and antioxidant activity (International Application Ser. No. PCT/US95/07404).

Recent research has also shown that Aloe vera, a term used to describe the extract obtained from processing the entire leaf, isolated from the *Aloe vera* species of Aloe can be used as a vehicle for delivering the corticosteroid, hydrocortisone, administered both topically and subcutaneously to the site of inflammation. (Davis et al. (1991) JAPMA 81:1). Davis et al. studied the topical and systemic anti-inflammatory activity of Aloe vera alone and in combination with hydrocortisone acetate. This study revealed that Aloe vera contributed in an additive way to the activity of the steroid, suggesting that Aloe vera may be useful as a biological vehicle for hydrocortisone. These studies also revealed that Aloe vera assists in the penetration of hydrocortisone through the stratum corneum. Davis has also shown that Aloe vera can be used as a biological vehicle for the delivery of the estrogenic hormones, estrogen and β-estradiol and androgenic hormone, testosterone propionate. (U.S. application Ser. No. 08/662,654, filed Jun. 13, 1996, entitled, "Method of Using Aloe Vera as a Biological Vehicle," now issued as U.S. Pat. No. 5,708,038, which is incorporated herein by reference in its entirety). The significance of these findings is that if used in combination with Aloe vera, the dosage of the steroid can be reduced, while maintaining its biological activity, thereby reducing or eliminating any toxic side effects associated with higher dosages. Since Aloe vera contains many hydrophilic compounds, such as enzymes, amino acids and carbohydrates, as well as, hydrophobic compounds, such as vitamins and sterols, Davis et al. postulate that pharmacologic agents of both solubilities can be placed in Aloe vera and carried through the epidermal barrier. (Davis et al. (1991) JAPMA 81:1).

SUMMARY OF THE INVENTION

The present invention includes a novel biological vehicle that can be used for the delivery of a variety of biologically active agents. The vehicle, called Maxcell™, is comprised of Aloe polysaccharide fraction Immuno-10 (see U.S. patent application Ser. No. 09/169,449, filed Oct. 9, 1998, entitled "Process for the Preparation of Immunomodulatory Polysaccharides from Aloe," which is incorporated herein by reference in its entirety), aqueous extract of *Ziziphus jujuba* fruits, hydrophilic solvent extract of *Glycyrrhiza uralensis* rhizome, organic solvent extract of *Piper nigrum* or *Piper longum*, and calcium inorganic and/or organic salts. The components of Maxcell™ combine to facilitate the harmony between biologically active agents and targeted cells and organs by guiding the biological active agents to their sites of action; by preventing the clearance of the agents from blood; and by protecting cells against harsh properties of biological active agents. The biological vehicle functions as a bioadhesive polymer that selectively binds to the active ingredients thereby forming a complex; the complex thus formed then selectively binds to mannose-6-phosphate receptors on the cell membrane. This serves to promote efficient delivery of the active ingredients to the target cells.

The biological vehicle of this invention can be used to deliver a variety of biologically active agents including, but not limited to nutrients and dietary supplements, such as essential minerals like iron, chromium, selenium, zinc, copper, magnesium, manganese, calcium; vitamins such as vitamins A, E, K and D, and vitamins B1, B2, B6 and B12; essential amino acids and derivatives thereof such as arginine, lysine, leucine, phenylalanine, taurine, and N,N-dimethyl glycine; anti-oxidants such as like bioflavonoids, polyphenols, beta-carotene, curcumine, catechins, anthocyanidins; hormones such as melatonin; single plant extracts such as like Echinacea, garlic, Gingko biloba, Goldenseal, Saw palmetto, Ginseng (Panex, Siberian, & American), Cat's claw Astragalus, St John's Wort; and combinations of the above nutrients and dietary supplements. The components of Maxcell™ not only function as a classical delivery system to target bioavailability, but also emphasize the response from the targeted living cells through renewal, enhancement and protection functions. Additionally, the components of Maxcell™ also combine to produce synergistic effects. Also included in the invention is a method for preparing the vehicle, methods for using the vehicle and nutritional supplement formulations containing the vehicle.

It is to be understood that both the foregoing general description and the following detailed description are exemplary and explanatory only and are not restrictive of the invention as claimed.

DETAILED DESCRIPTION OF THE INVENTION

The present invention describes a novel biological vehicle that can be used for the delivery of a variety of biologically active agents, including but not limited to nutrients, dietary supplements and other compounds with biological activity. The vehicle, called Maxcell™, is comprised of Aloe polysaccharide fraction Immuno-10, aqueous extract of *Ziziphus jujuba* fruits, hydrophilic solvent extract of *Glycyrrhiza uralensis* rhizome, organic solvent extract of *Piper nigrum* or *Piper longum*, and calcium inorganic and/or organic salts. The components of Maxcell™ combine to: enhance the therapeutic effects of the biologically active agents, enhance intracellular communication and response to biologically active agents, facilitate the transport of biologically active agents into the blood stream following ingestion, bind to and protect biologically active agents, guide the agents to their sites of action and prevent the clearance of the biologically active agents. The biological vehicle can be used to deliver a variety of biologically active agents, including but not limited to nutrients and dietary supplements, such as essential minerals like iron, chromium, selenium, zinc, copper, magnesium, manganese, calcium; vitamins such as vitamins A, E, K and D and vitamins B1, B2, B6 and B12; essential amino acids and derivatives thereof such as arginine, lysine, leucine, phenylalanine, taurine, and N,N-dimethyl glycine; anti-oxidants such as like bioflavonoids, polyphenols, beta-carotene, curcumine, catechins, anthocyanidins; hormones such as melatonin; single plant extracts such as like Echinacea, garlic, Gingko biloba, Goldenseal, Saw palmetto, Ginseng (Panex, Siberian, & American), Cat's claw Astragalus, St John's Wort; and combinations of the above nutrients and dietary supplements.

The components of Maxcell™ not only function to enhance bioavailability, but also combine to promote cell renewal, stimulate the immune system and confer protection against toxins and the side effects of drugs. Additionally, the components of Maxcell™ also combine to produce synergistic effects.

Certain terms used to describe the invention herein are defined as follows.

The term "Aloe" refers to the genus of South African plants of the Liliaceae family of which the *Aloe barbadensis* plant is a species.

The term "Aloe vera" is defined as the dried inner filet of the leaf of various species of the Aloe plant.

The term "Aloe vera polysaccharide," refers to polysaccharides isolated from the Aloe plant.

The term "Aloe vera polysaccharide fraction Immuno-10" also referred to as "Immuno-10," refers to a complex carbohydrate preparation produced from the inner filet of the leaf of Aloe species. It functions as a bioadhesive polymer by binding to and coordinating the active ingredients; the complex thus formed then selectively binds to receptors on the cell membrane. This serves to promote efficient delivery of the active ingredients to the target cells. In addition to drug delivery functions, Aloe vera polysaccharide fraction Immuno-10 has been shown to prevent the suppression of contact hypersensitivity in mice exposed to ultraviolet B radiation. Immuno-10 also inhibits ultraviolet B irradiation-induced tumor necrosis factor (TNF-α) release in a human epidermoid carcinoma cell line and promotes wound-healing and cellular proliferation, particularly in the immune system.

The typical process for the isolation of Aloe vera polysaccharide involves alcohol precipitation from the juice of *Aloe barbadensis*. The instant application makes use of a novel and more efficient procedure, described in the co-pending and commonly assigned U.S. patent application Ser. No. 09/169,449, filed Oct. 9, 1998, entitled "Process for the Preparation of Immunomodulatory Polysaccharides from Aloe," which is incorporated herein by reference in its entirety.

The composition and chemical structure of the activated polysaccharides in Immuno-10 was determined using pharmaceutical grade Immuno-10 having a purity of > 95% and is as follows:

Size exclusion chromatography analysis shows that the average molecular weight of the polysaccharides in Immuno-10 is 70~80 kDa with a range between 50~200 kDa. The molecular weight was determined using size exclusion chromatography on a Sephadex G-100 column and HPLC gel permeation on a Superose 12 column (H10/30 Pharmacia).

Analysis of the monosaccharide composition indicates that the polysaccharides in Immuno-10 contain D-galactose (approx 5% or less), D-glucose (approx 5% or less) and D-mannose (approximately 90%). The polysaccharides in Immuno-10 may also contain trace amounts of xylose and arabinose.

Proton and $^{13}$C NMR-spectroscopy analysis indicates that the monosaccharide linkages are primarily β-1,4 linkages. The main structure of Immuno-10 polysaccharide is β-1,4 glucomannan. Furthermore, the polysaccharide is highly acetylated (approximately 1 acetyl group per sugar residue on average). The 2, 3 and 6 positions of the monosaccharide units can be independently substituted with an —OH or an —OAc.

A "vehicle" refers to a substance which acts as a physical or physiological carrier for biologically active agents, also referred to as pharmacologic agents. A vehicle aids in the penetration of biologically active agents through physical barriers, such as the stratum corneum, gastrointestinal, respiratory, urinary and blood-brain barriers. A "biological vehicle" also enhances the biological activity of the active agent regardless of the agent under consideration. Thus, a biological vehicle not only acts as a carrier, but also has an additive or a synergistic effect as it enhances the effects of other pharmacologic agents. The vehicle of the instant invention is comprised of Aloe vera polysaccharide extract (preferably Immuno-10), cAMP, glycyrrhizinate, piperine alkaloids and calcium inorganic or organic salts.

The term "biologically active agent," also referred to as "pharmacologic agent," refers to any substance that can cause a physiological effect in a living organism. Biologically active agents may be derived from natural sources, such as extracts from plants and herbs, or they may be synthesized from precursor components in the laboratory. They include nutrients and nutritional supplements, including but not limited to amino acids, amino acid derivatives, vitamins (both water and fat soluble) and minerals, antioxidants, metabolic intermediates, co-enzymes, cofactors, hormones or any other nutritional supplement known in the art. Biologically active agents also include herb and plant extracts, including but not limited to Echinacea, garlic, Gingko biloba, Goldenseal, Saw palmetto, Ginseng, Gotu kola (*Centella asiatica*), Withania, Kava Kava, Astragalus, St John's wort; and compositions which contain combinations of the above nutrients and dietary supplements.

"Glycyrrhizinate" also referred to as "glycyrrhizinic acid" or its salts, including but not limited to its potassium and ammonium salts, is obtained from the rhizome of *Glycyrrhiza uralensis* and other species from the same genus. The glycyrrhizinic acid/salt content is typically from 5% to 98% in the crude or refined extract. The Glycyrrhiza species known as licorice, is one of the oldest traditional medicines and is used as a tonic, antiphlogistic, mucolytic, expectorant and analgesic for treatment of gastrointestinal and respiratory disorders. Glycyrrhizinic acid and its salts provide protection against rapid DNA damage and inhibit mutagenicity. They also provide protection against gastric ulcers induced by drugs and have been documented as having protective effects against toxins, viruses, tumors and allergic agents.

"Piperine alkaloids" are a mixture of nitrogen containing compounds existing in the fruit of *Piper longum* and *Piper nigrum*, both indigenous to India. These Ayurvedic herbs are well known as stimulant, carminative and tonic agents. Piperidine is one of the major piperine alkaloids in the hydrophobic extract. The piperidine content in the crude or refined extract is typically between 5% to 97%. Piperidine has been documented for its enhancement of drug bioavailability. It is believed that this effect is due to an increase in the permeability of intestinal epithelial cells, and also to the inhibition of drug metabolism pathways. Piperine alkaloids are also known to function as appetite stimulants, anti-colic and anti-tussive agents, and can induce resistance against infection.

"cAMP" (cyclic adenosine monophosphate) can be found in the largest amounts ever reported in the fruit of *Ziziphus jujuba*, where it is present at 100 to 1000 μmol/g. The fruits of *Ziziphus jujuba* have been utilized in traditional medicine to tonify the spleen, augment energy, nourish the blood and calm the spirit. cAMP is known as being one of the key molecules involved in intracellular signal transduction. cAMP is synthesized in cells in response to stimulation from certain hormones or biologically active agents. It binds to and activates a number of protein kinases, which are responsible for a myriad of cellular changes. cAMP has been implicated in switching the direction of nerve growth cone turning, immunostimulation, modulating leukocyte adhesion, modulating superoxide production in macrophages, modulating lipolysis and modulating tumor necrosis factor. Increased levels of cAMP in cells have been shown to potentiate hormonal response in vitro and in vivo and have been used as a treatment for selective weight control, neurodegenerative conditions, viral infections, allergic diseases, thrombosis, platelet aggregation, cardiovascular disease and high intraocular pressure. (See Song et al. (1997) Nature 388:275 Laudanna et al. (1997) J. Biol. Chem. 272:24141; Si et al. (1997) 36:1; Wang et al. J. Biol. Chem (1997) 272:5959; Hoffman et al. (1984 Am. J. Physiol. 274:E772).

"Calcium (inorganic and organic salts)" supply calcium as a nutritional supplement and are also believed to augment intracellular stores of calcium. Intracellular calcium is synergistic with cAMP as a second messenger during signal transduction. In this way, calcium is believed to potentiate and enhance cellular response to extracellular signals sent by biologically active agents.

In one embodiment of the instant invention, a biological vehicle is prepared by combining Aloe vera polysaccharide extract (preferably Immuno-10), isolated from *Aloe vera* gel, *Ziziphus jujuba* fruit extract containing cAMP, *Glycyrrhiza uralensis* rhizome extract containing glycyrrhizinate, *Piper nigrum* or *Piper longum* fruit extract containing piperine alkaloids and calcium inorganic or organic salts. In a preferred embodiment the individual components are combined respectively in substantially a 10:35:4:4:22 weight:weight ratio. The corresponding biologically active components are formulated respectively as Immuno-10:cAMP:glycyrrhizinate:piperine alkaloids:calcium in substantially a 2:0.005:6:1:10 weight:weight ratio.

The resulting biological vehicle may be administrated orally at approximately 100 to 2500 mg/day. In a preferred embodiment the vehicle is administrated at approximately 750 mg/day. The vehicle may be combined with any number of biological agents in order to supply said biological activities. In preferred embodiments, the vehicle and the active biological agents are combined, with the optional inclusion of pharmaceutically acceptable excipients, in the form of, but not limit to, capsules, tablets, soft gel capsules, time-release capsules and liposomes. In a preferred embodiment the amount of Maxcell™ in the composition is from 1% to 99.7% on a weight basis.

The biologically active agents can be nutrients and nutritional supplements, such as amino acids, vitamins and derivatives thereof, minerals, anti-oxidants, metabolic intermediates, co-enzymes and co-factors, hormones and derivatives thereof, or any other nutritional supplements known in the art. It is also possible to combine the biological vehicle with herb and plant extracts, including, but not limited to Echinacea, garlic, *Gingko biloba*, Goldenseal, Saw palmetto, Ginseng (Panex, Siberian and American), Gotu kola (*Centella asiatica*), Withania, Kava Kava, Astragalus, St John's wort, and compositions which contain combinations of the above nutrients and dietary supplements.

Example 1 describes one example of the preparation of the Maxcell™ vehicle.

Figure 1:
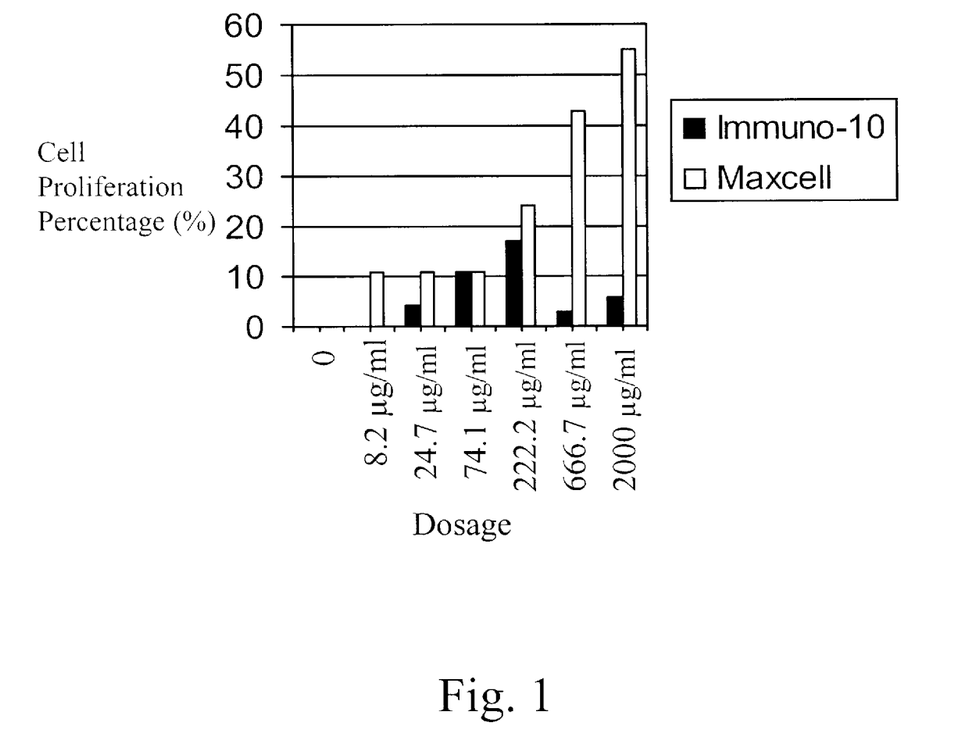
FIG. 1 illustrates the ability of Maxcell™ and Immuno-10 to stimulate kidney cell renewal (%) as a function of dosage in µg/mL.

Example 2 describes the ability of Maxcell™ to promote cell renewal. As can be seen in FIG. 1, at a concentration of 2 mg/mL, Maxcell™ stimulates kidney cell proliferation by 55%. When the Immuno-10 polysaccharide fraction (which is a component of Maxcell™) is tested alone in the same assay, only moderate stimulation (14% -17%) is observed. Therefore, it can be seen that the other ingredients in Maxcell™ act in concert with the Immuno-10 to promote kidney cell proliferation.

Figure 2:
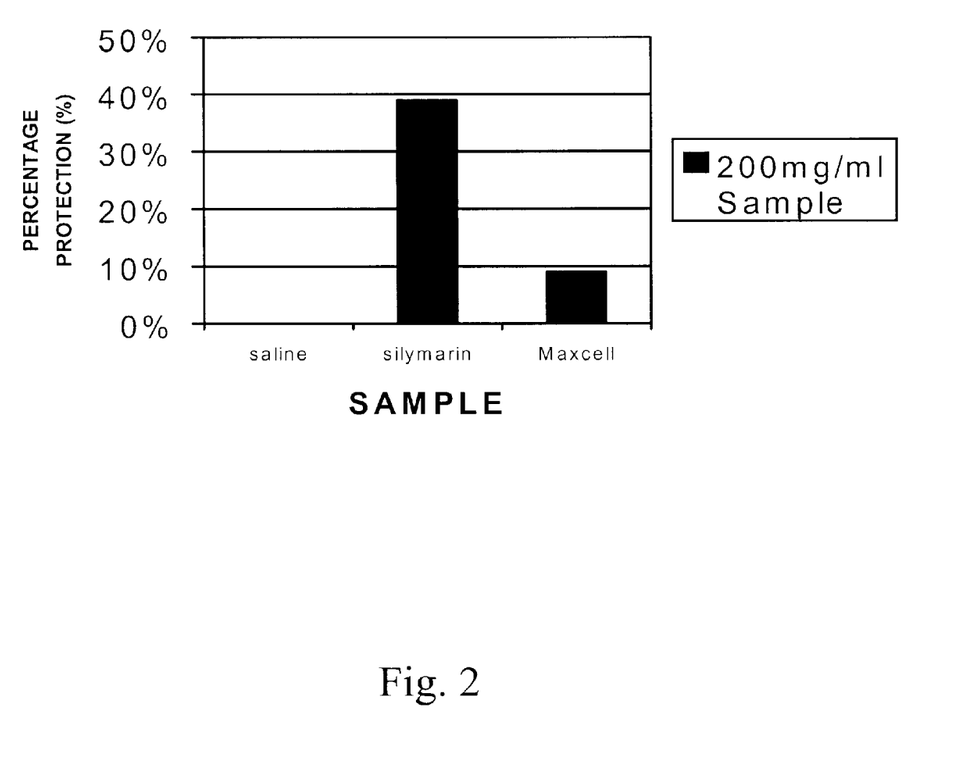
FIG. 2 illustrates the ability of Maxcell™ to protect the liver cells of mice against damage caused by high dosage of $CCl_4$.

Example 3 illustrates the ability of Maxcell™ to protect liver cells from damage caused by $CCl_4$ The results are set forth in FIG. 2.

Figure 3:
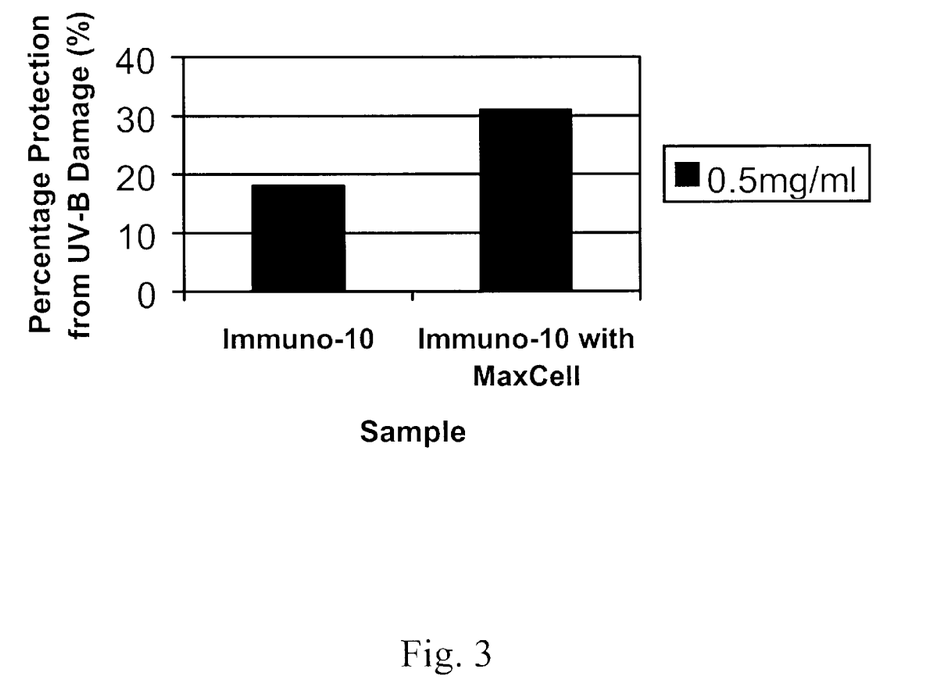
FIG. 3 illustrates the ability of Immuno-10 and Maxcell™ to protect cells against UV-B damage. Both Immuno-10 and Maxcell™ provide 18% to 31% protection of cells against UV-B damage.

The Maxcell™ vehicle also confers protection against ultraviolet B irradiation upon treated cells (Example 4). By monitoring the amount of TNF-α released following irradiation (a response to UV-B damage), it has been determined that Maxcell™ provides up to 31% more protection than control solutions (data not shown). FIG. 3 illustrates that Immuno-10 and Maxcell™ provide 18% to 31% protection of cells against UV-B damage, respectively.

Figure 4:
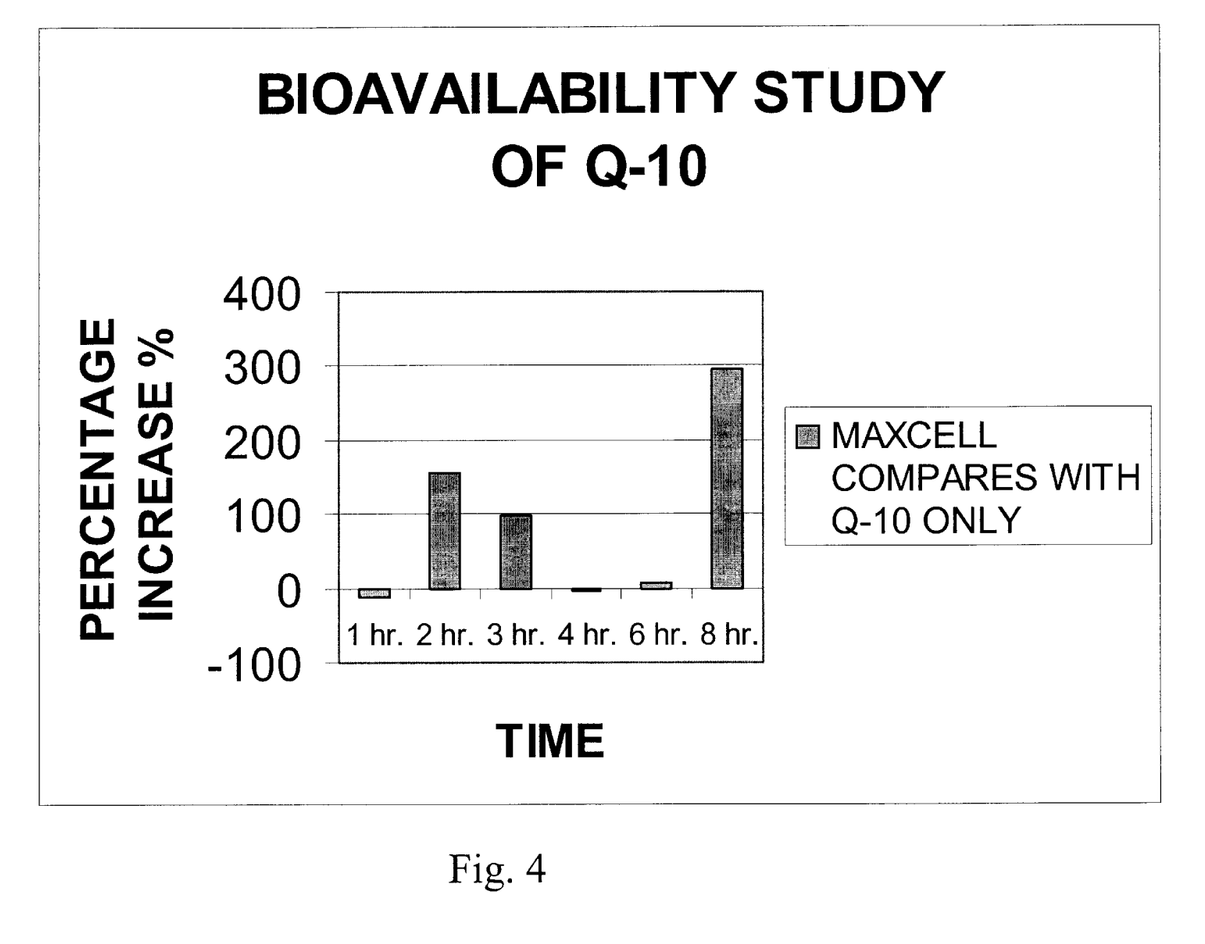
FIG. 4 illustrates Coenzyme Q-10 bioavailability enhancement by Maxcell™. This figure depicts the increase of rat serum Q-10 level (%) as a function of time.
Figure 5:
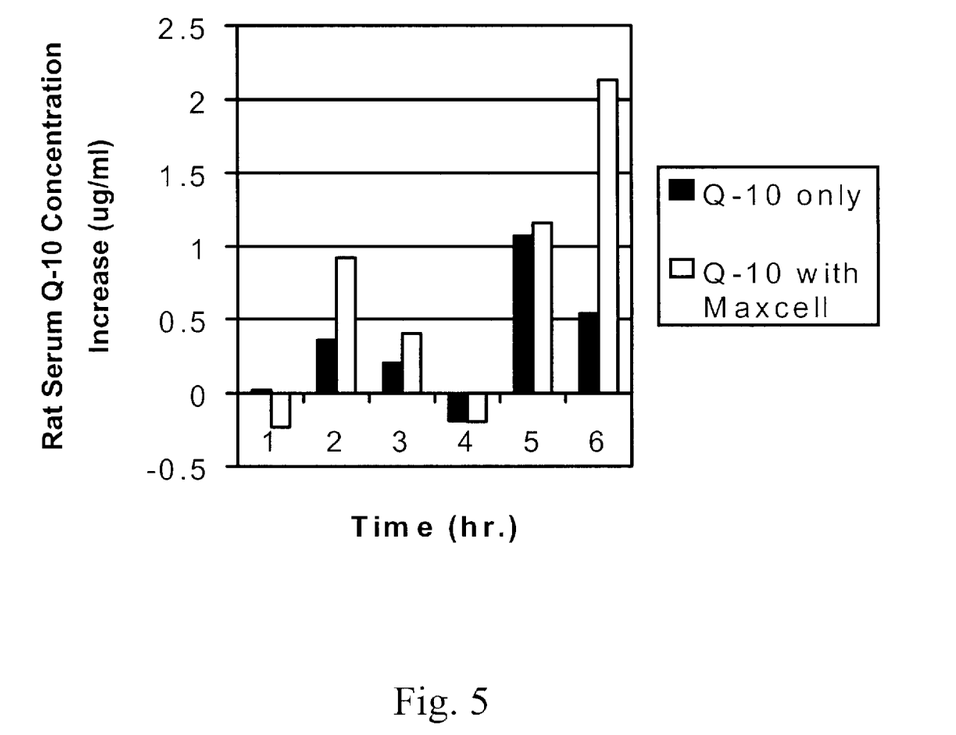
FIG. 5 illustrates Coenzyme Q-10 bioavailability enhancement by Maxcell™. This figure depicts the rat serum Q-10 concentration (µg/mL) increase as a function of time.
Figure 6:
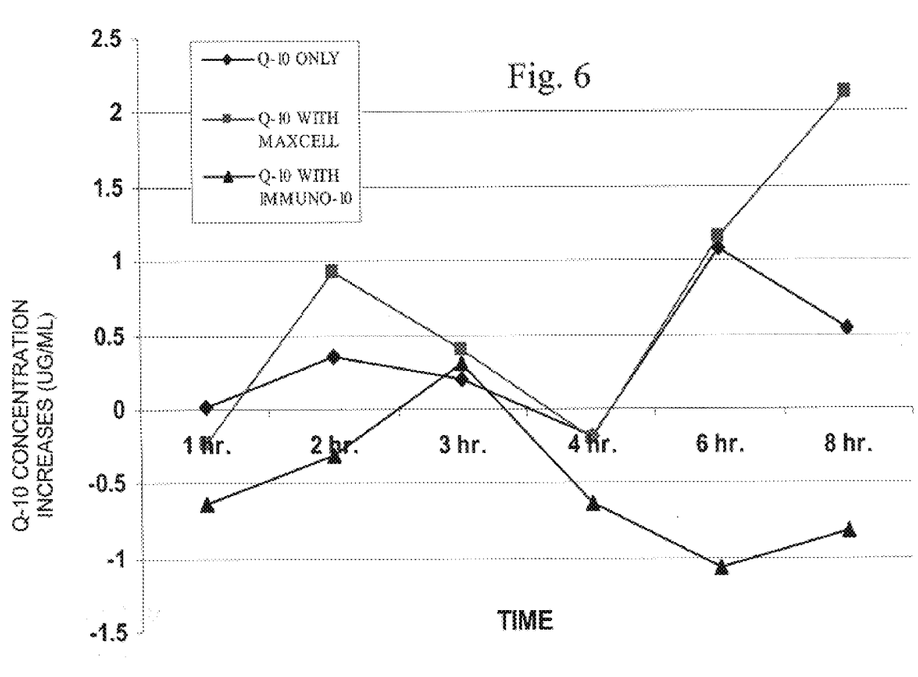
FIG. 6 illustrates graphically Coenzyme Q-10 bioavailability enhancement by Maxcell™. This figure depicts the rat serum Q-10 concentration (µg/mL) increase as a function of time for Q-10 only (♦), Q-10 in combination with Immuno-10 (■) and Q-10 in combination with Maxcell™ (∆).

Example 5 (FIGS. 4–6) illustrate the Coenzyme Q-10 (Q-10) bioavailability enhancement by Maxcell™. FIG. 4 illustrates the increase of rat serum Q-10 (%) levels as a function of time FIG. 5 illustrates the rat serum Q-10 concentration (μg/mL) increase as a function of time for Q-10 only and Q-10 in combination with Maxcell™. FIG. 6 depicts the rat serum Q-10 concentration (μg/mL) increase as a function of time for Q-10 only (♦), Q-10 in combination with Immuno-10 (■) and Q-10 in combination with Maxcell™ (Δ).

Example 6 describes the preparation of three different Maxcell formulations: the Bio Energy formulation, the Super Immune formulation, and the Anti-Stress formulation.

Figure 7:
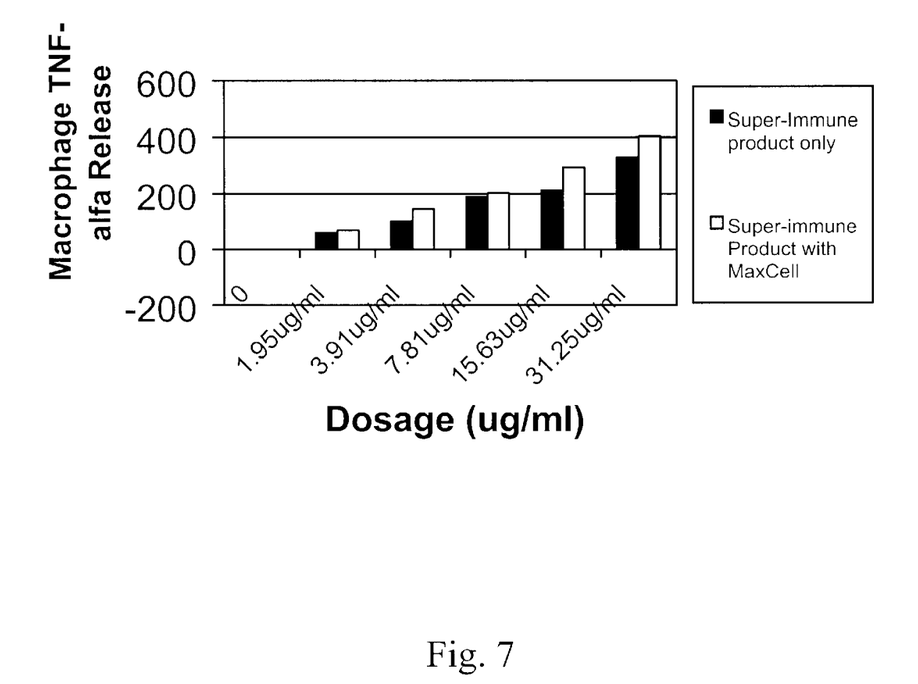
FIG. 7 illustrates graphically the combined effect of Maxcell™ and the Super Immune formulation on the stimulation of TNF-α release from mouse peritoneal macrophages. This figure depicts the release of TNF-α as a function of dosage.

Example 7 describes the method used to determine the combined effect of the Maxcell™ vehicle and the Super Immune formulation (Formulation 2, Example 6) on macrophage activation. The results are set forth in FIG. 7, which depicts the release of macrophage TNF-α measured as a function of dosage. As shown in FIG. 7, at all concentrations tested macrophage TNF-α release was increased by the Maxcell™ vehicle. This result demonstrates the effectiveness of Maxcell™ as a biological vehicle for the delivery of the Super Immune formulation.

Figure 8:
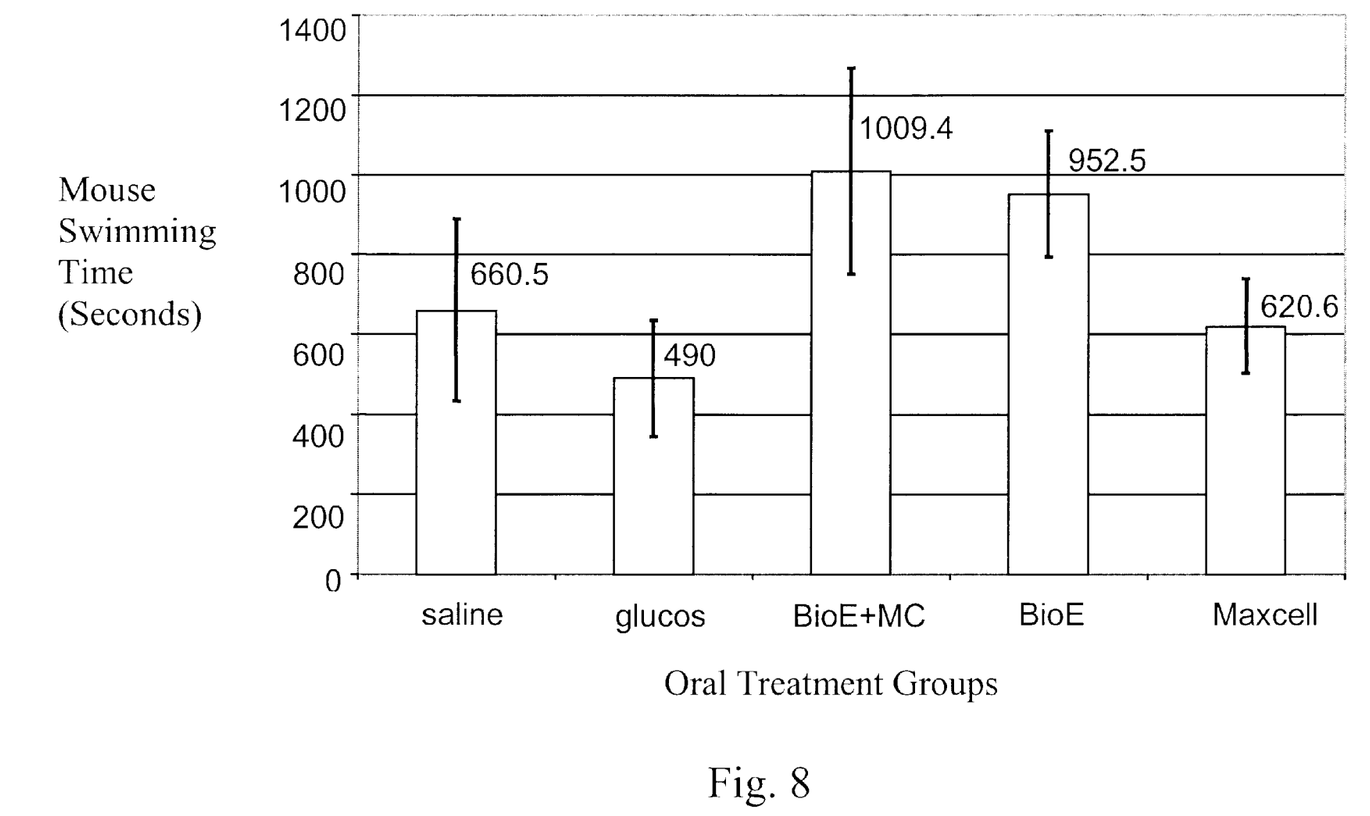
FIG. 8 illustrates the results of the Bio Energy (BioE) formulation Anti-Fatigue test.

Example 8 describes the method used to determine the effect of the Bio Energy formulation (BioE) on stamina and the combined effect of the Maxcell™ vehicle and the Bio Energy formulation (BioE) on stamina. The results are set forth in FIG. 8. As shown in FIG. 8, the Bio Energy formulation increases the stamina of the mice when compared to treatment with saline or glucose. Additionally, when used in combination with Maxcell™ the stamina of the mice is enhanced by virtue of the increase in bioavailability of the Bio Energy formulation.

The following examples are presented for illustrative purposes only and are not intended to limit the scope of the invention.

EXAMPLES

Example 1

Preparation of the Maxcell™ Vehicle

Extraction of *Ziziphus jujuba* fruit. *Ziziphus jujuba* fruit (purchased from the Pacific Ocean Grocery Store, Denver, Colo.) was dried and crushed in a coffee grinder. The product was then freeze dried at room temperature, then finely ground to a small particle powder with a total weight of 857 g. The powder was soaked in 4.5 L of distilled water for 2 hours at 60° C., then centrifuged at 3,000 rpm for 15 minutes at room temperature. The supernatant was filtered into an Erlenmeyer flask. The remaining plant residue was extracted again in the same manner and the two extract solutions were combined and lyophilized to yield 376.7 g of a yellow powder with a sweet taste.

Preparation of Maxcell™. 100 g of Aloe polysaccharide fraction Immuno-10, prepared as described in co-pending and commonly assigned U.S. patent application Ser. No. 09/169,449, filed Oct. 9, 1998, entitled "Process for the Preparation of Immunomodulatory Polysaccharides from Aloe," which is incorporated herein by reference in its entirety, was combined with 350 g Ziziphus extract, 40 g of solvent extract from *Piper nigrum,* 220 g calcium phosphate and 40 g of monoammonium glycyrrhizinate (>65% pure).

The daily dosage of this formulation (750 mg) provides 100 mg Immuno-10, 350 mg Ziziphus extract, 5 mg piperine extract, 245 mg calcium phosphate and 50 mg of monoammonium glycyrrhizinate (>65% pure).

Example 2

Stimulation of Cell Proliferation by Maxcell™

This experiment was performed using BHK-21:Baby Hamster Kidney cell line in DMEM (Dulbecco's modified eagle medium)/2.5~10% FBS with 3000~5000 cells/well. The cells were grown in a 96 well flat-bottom tissue culture treated plate. The MaxCell™ solution was prepared in DMEM/FBS/PGS at concentrations of 8.2 μg/mL, 24.7 μg/ml, 74.1 μg/mL, 222.2 μg/mL, 666.7 μg/mL and 2000 μg/mL. Fibroblast growth factor (FGF) was used as a positive control in DMEM/FBS/PGS at a concentration of 150 ng/mL. 200 μL of DMEM/FBS/PGS was added to all of the perimeter wells of the 96 well cell culture plate, as an experimental control. All experiments were performed in triplicate for FGF and MaxCell™ (6 doses each)/plate. The BHK cells were diluted to 3000~5000 cells/50 μL (harvested and counted prior to need) in DMEM/FBS/PGS. The samples were placed in a 37° C. incubator for three days, after which 25 μL/well of MTT was added to all sample and control wells. The plates were incubated plates for 4.5 additional hours followed by addition of 100 μL extraction solution in the dark, then placed on a wet paper towel and covered with foil at 37° C. The following day the plates were read on dual wavelength 570–630 nm. The result are set forth in FIG. 1.

Example 3

Protection of Liver Cells by MaxCell™

ICR mice, 8 weeks of age, were used in this experiment. The animals received food and water ab libitum. They were administrated MaxCell™ in saline at 200 mg/kg, silymarin in saline at 200 mg/kg, and saline only, intraperitoneally for 4 days. After the fourth dose the animals received an intraperitoneal injection of carbon tetrachloride (CCl$_4$) at 20 mg/kg in 0.2 mL to induce liver damage. After 24 hours of treatment with CCl$_4$, the animals were euthanized by CO$_2$ asphyxiation and blood was drawn by cardiac puncture into a heparinized syringe. The serum glutamic oxalacetic and glutamic pyruvic transminases levels were determined as described by Reitman and Frankel (1957) 28:56–63. The result are set forth in FIG. 2.

Example 4

Effect of MaxCell™ on Immuno-10 Protection against UV Radiation-Induced Local and Systemic Suppression of Inflammatory Responses This experiment was performed as described by Wolf et al. (1993) The Journal of Investigative Dermatology 100:254–259, which is incorporated herein by reference in its entirety. Wolf et al's experiment is as follows. UV radiation was provided by a bank of sic FS40 sunlamps (National Biology Corp., Twinsburg, OH), which have a peak emission at 313 nm and deliver 65% of their total energy within the UVB (280–320 nm)-wavelength range; their UVB irradiance was 5 W/m$^2$ at a 20-cm distance, as determined by an IL 200 radiometer equipped with an SEE 240 detector fitted with an SES280 filter and a quartz diffuser (International Light, Inc., Newburyport, MA). One day after the dorsal hair of the mice had been removed with electric clippers, they were exposed to the radiation source while housed five per cage in individual compartments. Because of shielding by the cage lids, the final irradiance received by the animals was approximately 3 W/m$^2$. The sunscreen preparations were liberally applied (approximately 200 μl/mouse) and rubbed on the shaved dorsal surface and tail of the mice 20 min before exposure to UVR. Measurement of Inflammatory Response. The inflammatory response was determined by measuring the double skin-fold thickness of the dorsal skin with a spring-loaded micrometer (Mitutoyo, Tokyo, Japan) prior to and 24 and 48 h after UVR exposure. Skin swelling was determined by substracting the average skin thickness before UV irradiation from that after UV irradiation. The protection from inflammation by a sunscreen was defined as complete protection where there was no significant skin swelling in a sunscreen-treated UV-irradiated group 24 and/or 48 h after UVR exposure when compared with sunscreen-treated, unirradiated mice; the protection was defined as partial protection when there was significant skin swelling, but the swelling was significantly different from that of the UC-irradiated group without suncreen.

The Immuno-10 was prepared as described in copending U.S. patent application Ser. No. 09/169,449, filed Oct. 9, 1998, entitled "Process for the Preparation of Immunomodulatory Polysaccharides from Aloe." The dosage of Maxcell™ and Immuno-10 was 0.5 mg/mL. The results are set forth in FIG. 3.

Example 5

Enhancement of the Bioavilability of Coenzyme Q (Q-10) by Maxcell™

CD male rats, 8 weeks of age, were used for this experiment. The animals were fasted 18 hours and cannulated. Water was provided ab libitum. Positive control animals (4 rats) received one oral dose of 50 mg/kg Q-10 in 400 μL of soy bean oil. Negative control animals (4 rats) received one oral dose of 50 mg/kg saline. Study animals (2×4 for each group) received one oral dose of 200 mg/mL of MaxCell™ (prepared as described in Example 1) or Immuno-10 (prepared as described in copending U.S. patent application Ser. No. 09/169,449, filed Oct. 9, 1998, entitled "Process for the Preparation of Immunomodulatory Polysaccharides from Aloe") with 50 mg/kg Q-10 in 400 μL of Soybean oil. Approximately 600 μL of blood was taken at 1, 2, 3, 4, 6, and 8 hours. The blood was analyzed to determine the amount of coenzyme Q in the plasma as described by Kaplan et al. (1995) Physiol. Res. 44:39–45. The results are set forth in FIGS. 4–6.

Example 6

Maxcell™ Formulations

Three different formulations using the instant biological vehicle (Maxcell™) were prepared. These formulations should be regarded solely as examples, and are not meant to limit the ways in which Maxcell™ may be used.

Formulation 1. Bio Energy

Dose: 3 tablets per day — Daily Dosage

| Component | Amount | Effective Range |
|---|---|---|
| Ginseng extract (Siberian and/or Panex) | 250 mg | 10–1,000 mg |
| Co-enzyme Q$_{10}$ | 18 mg | 5–250 mg |
| α-ketoglutaric acid | 300 mg | 50–1,000 mg |
| Potassium magnesium aspartate | 300 mg | 50–1,000 mg |
| Chromium polynicotinate | 300 μg | 50–1,000 μg |
| Maxcell™ | 750 mg | 100–2,500 mg |

Formulation 2. "Super Immune" Formulation

Dose: 3 capsules or tablets daily — Daily Dosage

| Component | Amount | Effective Range |
|---|---|---|
| Astragalus extract | 500 mg | 50–1,500 mg |
| Schisandra extract | 300 mg | 50–1,500 mg |
| Ganoderma extract | 150 mg | 50–1,000 mg |
| Maxcell™ | 750 mg | 100–2,500 mg |
| L-arginine | 200 mg | 50–1,000 mg |

The Schisandra extract contains schisandrins and the Ganoderma extract contains ganoderic acid and glucans.

Formulation 3. "Anti-Stress" Formulation

Tablet or capsule — Daily Dosage

Dose: 2–3 tablets per day

| Component | Amount | Effective Range |
|---|---|---|
| Ziziphus jujuba Mill var. spinosa seed extract | 200 mg | 50–600 mg |
| Gotu kola (Centella asiatica) whole plant extract | 200 mg | 50–600 mg |
| Withania somnifera root extract | 300 mg | 50–600 mg |
| Piper methylsticum rootstock extract | 200 mg | 50–500 mg |
| Taurine | 200 mg | 100–1,000 mg |
| Maxcell™ | 250 mg | 100–2,500 mg |

Example 7

Synergistic Effect of the Maxcell™ Vehicle on the Immune Stimulation Activity of the Super Immune Formulation This experiment was performed as described in copending U.S. application Ser. No. 09/169,449, filed Oct. 9, 1998, entitled "Process for the Preparation of Immunomodulatory Polysaccharides from Aloe," which is incorporated herein by reference in its entirety. Briefly, resident mouse peritoneal macrophages were isolated from ICR mice and plated at 200,000 cells per well in a 96-well plate. The cells were washed three times to remove non-adherent cells after a 2 hour incubation. The macrophages were then incubated with the Super Immune formulation, both with and without Maxcell™ overnight. The Maxcell™ vehicle was prepared as described in Example 1 and the Super Immune formulation was prepared as described in Example 6. Maxcell™ and the Super immune formulation were tested at 1.95 μg/mL, 3.91 μg/mL, 7.81 μg/mL, 15.63 μg/mL and 31.25 μg/mL. The TNF-α released into the media was determined by ELISA. Lipopolysaccharides (LPS) were used as a positive control. The results are set forth in FIG. 7.

Example 8

Improvement in Fatigue by the Bio Energy Formulation

ICR male mice, 8 weeks of age, were used for this experiment. The animals were fasted 18 hours prior to treatment with the Bio Energy formulation. Water was provided ab libitum. Positive control animals (8 mice) received one oral dose of 600 mg/kg glucose via gavage feeding. Negative control animals (8 mice) received one oral dose of 600 mg/kg saline via gavage feeding. Study animals (10 for each group) received 600 mg/mL of the BioEnergy formulation (prepared as described in Example 6) with MaxCell™, 600 mg/mL of the BioEnergy formulation without MaxCell™, and 134 mg/mL of MaxCell™ alone.

The animals received food and water ab libitum after being dosed. After 60 minutes, a 2 gram weight was glued to the end of the tails of the mice. Individual mice were placed into a tub (50 cm×30 cm×25 cm) of 20+/−0.5° C. water and allowed to swim until their heads went under water. The time of swim was recorded. The animals were then towel-dried and put into a warmed cage on top of a heating pad, until completely dry. The test results are depicted in FIG. 8.

What is claimed is:

1. A biological vehicle for the delivery of biologically active agents, said vehicle comprising Aloe vera polysaccharide, having the following characteristics:
   (a) comprised greater than >95% of polysaccharides, said polysaccharides in said composition having an average molecular weight of 70–80 kDa with a molecular weight range between 50–200 kDa;
   (b) said polysaccharides are comprised of D-galactose in amounts of approximately 5% or less, D-glucose in amounts of approximately 5% or less, and D-mannose in amounts of approximately 90%;
   (c) said polysaccharides are comprised of monosaccharides having primarily β-1,4 linkage; and
   (d) said polysaccharides are highly acetylated having approximately 1 acetyl group per monosaccharide, wherein said acetyl group is on the 2, 3, or 6 position of the monosaccharide unit, and
   piperine, cyclic adenosine monophosphate, calcium phosphate, and glycyrrhizin.

2. The vehicle of claim 1, wherein said polysaccharide, piperine, cAMP, calcium phosphate and glycyrrhizin are combined respectively in a weight-to-weight ratio that is substantially 2:1:0.005:10:6.

3. The vehicle of claim 1 wherein said Aloe vera polysaccharide is obtained from *Aloe barbadensis*.

4. The vehicle of claim 1 wherein said piperine is obtained from *Piper longum* or *Piper negrum*.

5. The vehicle of claim 1 wherein said cyclic adenosine monophosphate is obtained from the fruit of *Ziziphus jujuba*.

6. The vehicle of claim 1 wherein said glycyrrhizin is obtained from *Glycyrrgiza uralensis*.

7. The vehicle of claim 1 wherein said glycyrrhizin is monoammonium substituted.

8. A pharmaceutical composition comprising the vehicle of claim 1 and at least one biologically active biological agents in a biologically effective amount.

9. The pharmaceutical composition of claim 8 in the form of a capsule or tablet.

10. The pharmaceutical composition of claim 8 wherein said at least one biologically active biological agents are selected from the group consisting of plant extracts or nutritional supplements.

11. The pharmaceutical compound of claim 8 wherein said at least one biologically active biological agents are selected from the group consisting of amino acids, water soluble vitamins, fat soluble vitamins, co-enzyme $Q_{10}$, alpha ketoglutaric acid, minerals, antioxidants, or combinations of two or more of the above nutritional supplements.

12. The pharmaceutical compound of claim 8 wherein said at least one biologically active biological agents are selected from the group consisting of Panex Ginseng extract, Schisandra extract, Ganoderma extract, *Ziziphus jujuba* Mill var. *spinosa* seed extract, Gotu kola extract, *Withania somnifera* root extract, and *Radix polygalae* extract.

13. The compound of claim 1 further comprising L-tyrosine or a derivative thereof.

14. A method of using a composition comprising Aloe vera polysaccharide having the following characteristics:
   (a) comprised greater than >95% of polysaccharides, said polysaccharides in said composition having an average molecular weight of 70–80 kDa with a molecular weight range between 50–200 kDa;
   (b) said polysaccharides are comprised of D-galactose in amounts of approximately 5% or less, D-glucose in amounts of approximately 5% or less, and D-mannose in amounts of approximately 90%;
   (c) said polysaccharides are comprised of monosaccharides having primarily β-1,4 linkage; and
   (d) said polysaccharides are highly acetylated having approximately 1 acetyl group per monosaccharide, wherein said acetyl group is on the 2, 3 or 6 position of the monosaccharide unit, and
   piperine, cyclic adenosine monophosphate, calcium phosphate, and glycyrrhizin as a vehicle for the delivery of biologically active agents to a living organism, the method comprising administering an effective amount of said biologically active agents in combination with said composition.

* * * * *